United States Patent [19]

Ohnuma et al.

[11] Patent Number: 4,997,931

[45] Date of Patent: Mar. 5, 1991

[54] EPIPODOPHYLLOTOXIN GLYCOSIDES

[75] Inventors: Takeshi Ohnuma, Tokyo; Hideaki Hoshi, Chiba, both of Japan

[73] Assignee: Bristol-Myers Squibb Company, New York, N.Y.

[21] Appl. No.: 536,925

[22] Filed: Jun. 11, 1990

[51] Int. Cl.$^5$ .................. A61K 31/70; C07H 11/04; C07H 15/00

[52] U.S. Cl. ......................... 514/27; 514/35; 536/17.1; 536/18.1; 536/18.2

[58] Field of Search ............ 514/27, 35; 536/17.1, 536/18.1, 18.2

[56] References Cited

U.S. PATENT DOCUMENTS 3,524,844  8/1970  Keller-Juslen et al. ............ 536/18.1

4,904,768  2/1990  Saulnier et al. .................... 536/17.1

OTHER PUBLICATIONS

*J Med. Chem.*, 1971, 14:936–940.
*Chem. Lett.*, 1987, 799–802.
Watanabe et al., Carb. Res. 154:165–176 (1986).

*Primary Examiner*—Ronald W. Griffin
*Assistant Examiner*—Nancy S. Carson
*Attorney, Agent, or Firm*—Mollie M. Yang

[57] ABSTRACT

The present invention relates to novel antitumor compounds which are 4'-demethylepipodophylloxtoxin derivatives. More particularly, the novel compounds are 4'-demethylepipodophyllotoxin allopyranosides, allofuranosides, and mannopyranosides.

9 Claims, No Drawings

EPIPODOPHYLLOTOXIN GLYCOSIDES

BACKGROUND OF THE INVENTION

The present invention relates to novel antitumor compounds, their use in inhibiting tumor growth, and pharmaceutical compositions containing them. More particularly, the novel compounds are derivatives of 4'-demethylepipodophyllotoxin glucoside.

Etoposide and teniposide are two derivatives of 4'-demethylepipodophyllotoxin glucoside. The clinical efficacy of etoposide and teniposide in the treatment of a variety of cancers has been well documented and etoposide is currently approved in the United States for the treatment of small cell lung cancer and testicular cancer. The favorable therapeutic and pharmacological profiles of etoposide and teniposide have encouraged much activity in the search for other active analogs within the same class.

Most of the reported analogs and derivatives of etoposide and teniposide contain a D-glucose moiety, although a few derivatives having a different sugar are also known. For example, three D-galactopyranosides were reported in *J. Med. Chem.*, 1971, 10:936-40 and several L-glucopyranosides have been described in *Chem. Lett.*, 1987, 799-802. It is thus apparent that the effect of different sugar substituent on the activity of epipodophyllotoxin derivatives has not been fully explored.

Research effort by the present inventors in this area has led to the novel analogs disclosed and claimed herein. These new derivatives are distinguished over known 4'-demethylepipodophyllotoxin glycosides in having a mannose or an allose moiety. The novel compounds exhibit good activity against experimental leukemia in animal test models.

SUMMARY OF THE INVENTION

The present invention provides novel antitumor compounds of formula I

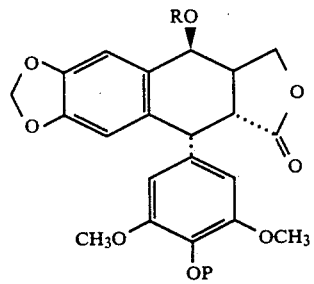

wherein R is selected from the group consisting of 4,6-O-alkylidene-β-D-allopyranosyl, 4,6-O-alkylidene-β-D-mannopyranosyl, 4,6-O-alkylidene-α-D-mannopyranosyl and 5,6-O-alkylidene-β-D-allofuranosyl; P is hydrogen or —PO$_3$H$_2$ or a pharmaceutically acceptable salt thereof.

DETAILED DESCRIPTION OF THE INVENTION

As used herein, unless otherwise specified, the term "alkylidene" refers to the portion of the cyclic acetal/ketal derived from an aldehyde or a ketone, and having from one to six carbon atoms in which the carbon chain may be straight or branched "Alkylidenate" refers to the formation of the cyclic acetal/ketal, i.e. reaction with the 4,6-diol of a pyranose, or the 5,6-diol of a furanose, with a carbonyl compound "Pharmaceutically acceptable salt" includes, but is not limited to, alkali metal salts such as sodium, potassium and lithium salts; alkaline earth metal salt such as magnesium and calcium salts; and salts with ammonia or a tertiary amine such as triethylamine.

The 4'-demethylepipodophyllotoxin glycosides of the present invention are prepared by condensing 4'-protected 4'-demethylepipodophyllotoxin (hereinafter also referred to as the protected aglycone) with an appropriately protected sugar. 4'-Protected 4'-demethylepipodophyllotoxins are known in the art; for example, 4'-benzyloxycarbonyl-4'-demethylepipodophyllotoxin and its preparation are described in U.S. Pat. No. 3,524,844. The choice of the phenol protecting group is not critical and may include the formation of ethers, acetals, and acyl derivatives such as esters or carbonates and the like.

The sugar starting materials may be prepared using methods generally available in the art. For example, 3-O-benzyl-allopyranose may be prepared by the method described by Dick et al in *Carbohydr. Res.*, 1975, 42:55-63; 2,3,4,6-O-tetraacetyl mannopyranose may be prepared by the method described by Watanabe et al in *Carbohydr. Res.*, 1986, 154:165-176. Again, the choice of protecting groups for the sugar hydroxy groups is not particularly restricted and may include other acyl groups such as formyl, propionyl haloacetyl and benzoyl groups. A mixture of the α- and β-anomers or the individual anomers may be used as the sugar starting material.

The allose and mannose starting material may be first converted to the respective alkylidenated derivative which is then condensed with the protected aglycone; or alternatively, the sugar may first be condensed with the protected aglycone followed by alkylidenation. The order in which these two steps are carried out is not critical As an example of the first method, 3-O-benzylallopyranose, with the anomeric hydroxyl group protected, is reacted with an aldehyde or ketone having one to six carbon atoms, or an acetal or a ketal thereof, in the presence of an acid such as toluenesulfonic acid to effect the formation of the cyclic acetal/ketal. The reaction is carried out at room temperature in a reaction inert solvent such as methylene or ethylene chloride The 2-O-hydroxyl group may be protected with a conventional protecting group, e.g. treatment with a base such as sodium hydride followed by benzyl bromide introduces the benzyl group.

A convenient protecting group for the anomeric hydroxyl group is the allylic group which may be introduced by reacting the sugar with allyl alcohol, in the presence of a mineral acid such as hydrochloric acid, at elevated temperature, e.g. the refluxing temperature of the reaction mixture. This reaction yields as products both allyl allopyranoside and allyl allofuranoside which can be separated by chromatography, and each used individually or in a mixture for the glycosidation of the protected aglycone. The allylic protecting group may be removed by the method of Corey et al, (*J. Org. Chem.*, 1973, 38:3224) which involves treating the compound with a rhodium reagent such as tris(triphenylphosphine)rhodium chloride, followed by hydrolysis. The alkylidenated sugar may be used for the glycosidation reaction that is described immediately below.

As an example of condensation between a sugar, and the protected aglycone, mention can be made of the use of 2,3,4,6-tetra-O-acetyl mannose. This glycosidation reaction is carried out in a reaction inert organic solvent, for example methylene or ethylene chloride at a temperature below 0° C., and in the presence of a catalyst such as boron trifluoride ethyl etherate. The sugar reactant and boron trifluoride ethyl etherate are used in at least equimolar amount relative to the aglycone; but preferably they are used in excess of from about 1.5 to about 5 equivalents relative to the aglycone The reaction time may be from minutes to about 2 hours depending on the nature of the reactants. The action of boron trifluoride ethyl etherate may be quenched by the addition to the reaction mixture a tertiary amine such as pyridine or triethylamine.

Following the condensation, the sugar protecting groups may be removed by conventional deblocking methods, e.g. acetyl groups may be conveniently removed by treatment with zinc compound such as zinc acetate. After the removal of the sugar hydroxy protecting groups, alkylidenation may be accomplished in a manner as previously described.

The condensation product obtained by either of the above described methods may be a mixture of α- and β-glycosides, in which case the mixture may be separated into the two anomers and each is then deprotected to remove the 4'-phenol protecting group, or the mixture of anomers may be deprotected first followed by separation of the deprotected products; the order is not critical. Separation of anomers may be effected by conventional techniques such as column chromatography.

Deprotection of the phenol may be accomplished using art-recognized methods and the choice of which depends on the nature of the protecting group. For example, the benzyloxycarbonyl protecting group may be removed by hydrogenation in the presence of a palladium catalyst. Compounds of formula I wherein P is hydrogen thus obtained may be further derivatized to provide the corresponding 4'-phosphate (compounds of formula I wherein P is $-PO_3H_2$). This may be accomplished by using known methods for converting a hydroxy group into its phosphate ester. Such methods include reacting a compound of formula I wherein P is hydrogen with a phosphorylating agent such as phosphorous oxychloride followed by hydrolysis to afford the phosphate product; or reacting the former with diphenyl chlorophosphate followed by catalytic hydrogenation to generate the phosphate ester. Pharmaceutically acceptable salts may be obtained by treating the acid with a base such as an alkali metal carbonate, bicarbonate or hydroxide.

BIOLOGICAL ACTIVITY

Representative compounds of the present invention were evaluated for in vitro cytotoxicity, and in vivo antitumor activity in mice.

In vitro cytotoxicity

Murine melanoma B16-F10 cells were grown and maintained at 37° C. under a humidified atmosphere in a 5% $CO_2$ incubator in Eagle's MEM medium (Nissui) containing kanamycin (60 µg/ml), and supplemented with heat inactivated fetal calf serum (10%) and nonessential amino acids (0.6%). Exponentially growing B16-F10 cells were harvested, counted and suspended in the culture medium at a concentration of $2.0 \times 10^4$ cells/ml. Twenty-four hours after planting cell suspension (180 µl) into wells of a 96-well microtiter plate, test materials (20 µl) were added to the wells and the plates were incubated for 72 hours. The cytotoxic activity against B16-F10 cells was colorimetrically determined at 540 nm after staining viable cells with neutral red solution.

In vivo antitumor activity

Antitumor activity of representative compounds of the present invention was tested in the lymphocytic leukemia P388 system. Female $CDF_1$ mice were inoculated intraperitoneally with $1.0 \times 10^6$ of leukemia cells per mouse (day 0) and test materials were intraperitoneally administered to mice once on day 1 (Q1D×1). Treated animals were observed for 45 days. The median survival time (MST) of each test group was recorded, and antitumor activity was expressed by means of T/C% values calculated by the following equation:

$$T/C\% = (MST\ treated \div MST\ control) \times 100$$

The T/C% values of over 125% are considered significant antitumor activity.

The results of the in vitro cytoxicity assay and in vivo antitumor evaluation are summarized in Table 1. For the in vivo expermient, only the maximum T/C% and the dose giving the maximum value are shown.

TABLE 1

| | In vitro cytotoxicity and in vivo activity against murine P388 leukemia | | |
|---|---|---|---|
| Compound | Cytotoxicity ($IC_{50}$, µg/ml) | Anti-P388 Dose (mg/kg/Day) | T/C % |
| Example 1 | 2.1 | 60 | 280 |
| Example 2 | | | |
| (epimer I) | >100 | 120 | 150 |
| (epimer II) | >100 | 60 | 140 |
| Example 3 | 0.12 | 30 | 186 |
| Example 4 | 19 | 10 | 124 |
| Etoposide | 0.21 | 120 | 288 |

The test results indicate that compounds of the present invention are useful as antitumor compounds. Accordingly, the present invention provides a method for inhibiting mammalian tumors which comprises administering an effective tumor-inhibiting dose of an antitumor compound of formula I to a tumor bearing host. For this purpose, the drug may be administered by conventional routes including, but not limited to, intravenous, intramuscular, intratumoral, intraarterial, intralymphatic, and oral; intravenous administration is preferred.

A further aspect of the present invention provides a pharmaceutical composition which comprises a compound of formula I and a pharmaceutically acceptable carrier. The antitumor composition may be made up of any pharmaceutical form appropriate for the desired route of administration. Examples of such compositions include solid compositions for oral administration such as tablets, capsules, pills, powders and granules, liquid compositions for oral administration such as solutions, suspensions, syrups or elixirs and preparations for parenteral administration such as sterile solutions, suspensions or emulsions. They may also be manufactured in the form of sterile solid compositions which can be dissolved in sterile water, physiological saline or some other sterile injectable medium immediately before use.

Optimal dosages and regimens for a given mammalian host can be readily ascertained by those skilled in the art. It will, of course, be appreciated that the actual dose used will vary according to the particular composition formulated, the particular compound used, the mode of application and the particular site, host and disease being treated. Many factors that modify the action of the drug will be taken into account including age, weight, sex, diet, time of administration, route of administration, rate of excretion, condition of the patient, drug combinations, reaction sensitivities and severity of the disease.

The following examples are only meant to illustrate the invention and are not to be construed as in any way limiting the scope of the invention which is defined solely by the claims appended to the specification.

PREPARATION OF STARTING MATERIALS

Preparation I. Allyl 3-O-benzyl-$\beta$-D-allopyranoside (compound A) and allyl 3O-benzyl-$\beta$-D-allofuranoside (compound B).

Dry hydrogen chloride (ca. 1 mol) was bubbled into a solution of 25.5 g (0.904 mol) of 3-O-benzylallopyranose (prepared according to the method described in W. E. Dick, et al, *Carbohydr. Res.*, 1975, 42:55) in 500 ml of allyl alcohol. The mixture was heated at 70° C. for 1 hour and then evaporated to dryness. The residue was chromatographed 4 times on a silica gel column (Wako gel C-200, 250 g). The column was finally eluted with chloroform and then chloroform-methanol (50:1-25:1) to separate 3 components.

Fractions showing a spot at Rf 0.70 (as monitored by TLC, CHCl$_3$:MeOH =20:1) were pooled and evaporated to dryness to give 3.43 g (14.5%) of 3-benzyl-1,6-anhydrohexopyranose as colorless crystals MP 112°-113° C.

Fractions showing a spot at Rf 0.60 (as monitored by TLC, CHCl$_3$:MeOH =20:1) were pooled and evaporated to dryness to give 2.33 g (8%) of allyl 3-O-benzyl-$\beta$-allofuranoside (compound B) as colorless crystals. MP 84°-85° C.

IR $\nu_{max}$(KBr) cm$^{-1}$ 3521, 1131, 1072.

$^1$H NMR (CDCl$_3$) $\delta$5.01 (1H, s, H-1).

Anal. Calcd. for C$_{16}$H$_{22}$O$_6$: C 61.92, H 7.15. Found: C 61.78, H 7.13.

Fractions showing a spot at Rf 0.50 (as monitored by TLC CHCl$_3$:MeOH=20:1) were pooled to give a mixture of allyl 3-O-benzyl-$\beta$-allofuranoside and allyl 3-O-benzyl-$\beta$-D-allopyranoside (compound A) (3.66 g, 12.5%).

The slowest-moving fractions were collected and evaporated to dryness to give 4.1 g (14%) of allyl 3-O-benzyl-$\beta$-D-allopyranoside (compound A) as an oil.

$^1$H NMR (CDCl$_3$) $\delta$4 75 (1H, d, J=7.7 Hz, H-1), 3.54 (1H, dd, J=7.7 and 2.6 Hz, H-2), 4.11 (1H, t, J=2.9 Hz, H-3), 3.62 (1H, dd, J=9.2 and 2.9 Hz, H-4), 3.67 (1H, m, H-5, 3.74 (1H, dd, J=11.7 and 4.8 Hz, Hax-6), 3.86 (1H, dd, J=11.7 and 2.9 Hz, Heq-6).

Preparation II. Allyl 2,3-di-O-benzyl-4,6-O-ethylidene-$\beta$-D-allopyranoside (compound C) and allyl 2.3-di-O-benzyl-5,6-O-ethylidene-$\beta$-D-allofuranoside (compound D)

To a solution of 3.66 g (0.0118 mol) of a mixture of compound A and compound B and 1,1-dimethoxyethane (4 ml) in 50 ml of dichloromethane was added 100 mg of p-toluenesulfonic acid, and the mixture was stirred at room temperature for 16 hours. The mixture was washed successively with aqueous sodium bicarbonate, water, and brine and dried over magnesium sulfate. The dried extract was evaporated to dryness, and the oily residue was chromatographed on a silica gel column (Kiesel gel 60, 50 g) using toluene-ethyl acetate (10:1) as eluant. The eluate was monitered by TLC and collected in 15-ml fraction. Fractions containing the desired products were combined and evaporated to dryness to give 2.25 g (56.5%) of a mixture of allyl 3-O-benzyl-4,6-O-ethylidene-$\beta$-D-allopyranoside and allyl 3-O-benzyl-5,6-O-ethylidene-$\beta$-D-allofuranoside.

Sodium hydride (482 mg, 10 mmol, about 60% in oil) was added to a solution of the above mixture (2.25 g, 6.7 mmol) in dimethylformamide (20 ml). The mixture was stirred at room temperature for 30 minutes, and then benzyl bromide (1 ml, 10 mmol) was added thereto, and stirring continued at room temperature for 30 minutes. After the addition of methanol (5 ml), the mixture was evaporated to dryness. The residue was extracted with 100 ml of ethyl acetate, washed with water and then brine, and dried over magnesium sulfate The dried extract was evaporated to dryness, and the residue was chromatographed on a silica gel column (Kiesel gel 60, 50 g) using toluene-ethyl acetate (10:1) as eluant. The eluate was monitored by TLC and collected in 15-ml fraction.

The faster-moving fractions (Nos. 17-33) were combined and evaporated to dryness to give 1.56 g (54.5%) of allyl 2,3-di-O-benzyl-4,6-O-ethylidene-$\beta$-D-allopyranoside (compound C) as an oil.

$^1$H NMR (CDCl$_3$) $\delta$4.91 (d, J=8.1 Hz, H-1).

The slower-moving fractions (Nos. 34-39) were combined and evaporated to dryness to give 930 mg (32.5%) of allyl 2,3-di-O-benzyl-5,6-O-ethylidene-$\beta$-D-allofuranoside (compound D) as an oil.

$^1$H NMR (CDCl$_3$) $\delta$5.05 (1H, d, J=1.6 Hz, H-1).

Preparation III.
2,3-Di-O-benzyl-4,6-O-ethylidene-D-allopyranose (compound E)

A mixture of 1.426 g (3.3 mmol) of compound C and 100 mg of tris(triphenylphosphine)rhodium chloride in 20 ml of ethanol, 10 ml of acetonitrile, and 3 ml of water was refluxed for 16 hours with stirring, concentrated to 5 ml, and extracted with 50 ml of ethyl acetate The extract was washed with water and brine and dried over magnesium sulfate. After removal of the solvent, an oily residue was chromatographed on a silica gel column (Kiesel gel 60, 20 g) using toluene-ethyl acetate (20:1) as eluant. The eluate was monitored by TLC and collected in 15-ml fraction. Fractions containing the desired product were combined and evaporated to dryness to give 970 mg (75%) of 1-propenyl 2,3-di-O-benzyl-4,6-O-ethylidene-$\beta$-D-allopyranoside as an oil.

To a stirred mixture of 1-propenyl 2,3-di-O-benzyl-4,6-O-ethylidene-$\beta$-D-allopyranoside (970 mg, 2.28 mmol) and mercuric oxide yellow (1 g) in a mixture of 20 ml of acetone and 2 ml of water was added a solution of mercuric chloride (0.8 g, 2.95 mmol) in 10 ml of acetone and 1 ml of water, and the mixture was stirred at room temperature for 30 minutes. The precipitate was removed by filtration, and the filtrate was concentrated to 5 ml and extracted with 50 ml of ether. The extract was washed with water and brine and dried over magnesium sulfate. The dried extract was evaporated to dryness, and the residue was chromatographed on a silica gel column (Kiesel gel 60, 50 g) using chloroform as eluant. Fractions containing the desired product (as monitored by TLC toluene-ethyl acetate 2:1, Rf 0.4)

were pooled and evaporated to dryness to give 800 mg (91%) of the title compound as a mixture of α- and β-anomers. (This mixture of α- and β-anomers will be referred to as compound E.)

$^1$H NMR (CDCl$_3$) δ5.16 (0.8H, d, J=4.0 Hz H-1, β-anomer), 5.17 (0.2H, d, J=8.1 Hz, H-1, β- anomer), 1.38 (2.4H, d, J=5.13 Hz, H-8, α-anomer), 1.37 (0.6H, d, J=5.13 Hz, H-8, β-anomer).

Preparation IV.
2,3-Di-O-benzyl-5,6-O-ethylidene-D-allofuranose (mixture of stereoisomers, compound F)

According to the procedure described in Preparation III, compound D (0.9 g) was converted to the title compound (450 mg) as an inseparable mixture of 4 stereoisomers based on the C-1" and C-7" positions (This mixture of isomers will be referred to as compound F.) The $^1$H NMR spectrum is as follows:

$^1$H NMR (CDCl$_3$) δ5.35 and 5.33 (0.25H, each d, J=1.5 Hz, Hα-1), 5.27 and 5.25 (0.75H, each d, J=4.4 Hz, Hβ-1) 5.03 and 5.04 (0.25H, each q, J=5.1 Hz, H-7 of β-anomer), 5.06 and 4.95 (0.75H, each q, J=5.1 Hz, H-7 of α-anomer) 1.36 and 1.32 (0.75H, each d, J=5.1 Hz, H-8 of β-anomer), 1.34 and 1.33 (2.25H, each d, J=5.1 Hz, H-8 of α-anomer).

SPECIFIC EMBODIMENTS OF THE INVENTION Example 1.
4'-Demethyl-4-O-(4,6-O-ethylidene-β-D-allopyranosyl)epidpodophyllotoxin

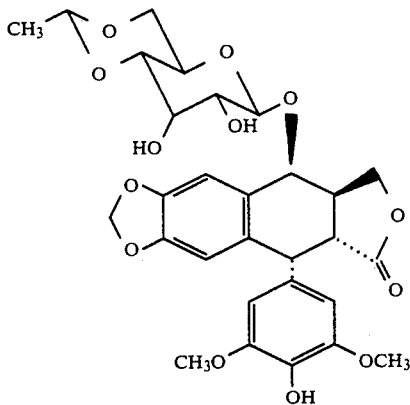

(a) preparation of 4'-O-benzyloxycarbonyl-4'-demethyl-4-O-(2,3-di-O-benzyl-4,6-O-ethylidene-β-D-allopyranosyl) epipodophyllotoxin To a cooled (−23° C.) and stirred solution of 4'-O-benzyloxycarbonyl-4'-demethylepiodophyllotoxin (534 mg, 1 mmol) and compound E (780 mg, 2 mmol) in 1,2-dichloroethane (50 ml) was added boron trifluoride etherate (0.5 ml 4 mmol). The mixture was stirred at −20° C. for 1 hour, and pyridine (0.3 ml) was added thereto, and stirring continued for 10 minutes. The mixture was then extracted with chloroform, washed with water and brine, and dried over magnesium sulfate. The dried extract was evaporated to dryness, and the residue was chromatographed on a silica gel column (Kiesel gel 60, 50 g) using toluene-ethyl acetate (10:1) as eluant, and the eluate was collected in 15-ml fraction. Fractions containing the desired product (Fractions 19-27) were combined and evaporated to dryness The residue was triturated with ether-cyclohexane to give 735 mg (81%) of 4'-O-benzyloxycarbonyl-4'-demethyl-4-O-(2,3-di-O-benzyl-4,6-O-ethylidene-β-D-allopyranosyl)epipodophyllotoxin. MP 150°-153° C. (dec.).

IR ν$_{max}$ (KBr) cm$^{-1}$ 1777, 1606, 1484, 1235, 1132, 1042.

UV λ$_{max\ (MeOH)}$ nm (ε) 291 (4,000)

Anal. Calcd. for C$_{51}$H$_{50}$O$_{15}$: C 67.84, H 5.58. Found: C 67.91, H 5.62.

(b) Preparation of 4'-demethyl-4-O-(4,6-O-ethylidene-β-D-allopyranosyl)epipodophyllotoxin A mixture of 4'-O-benzyloxycarbonyl-4'-demethyl-4-O-(2,3-di-O-benzyl-4,6-O-ethylidene-β-D-allopyranosyl)epipodophyllotoxin (500 mg, 0.55 mmol) and 10% palladium on carbon (500 mg) in 8 ml of acetic acid and 2 ml of ethanol was hydrogenated at room temperature for 24 hours under one atmospheric pressure. The catalyst was removed by filtration and washed twice with 10 ml of methanol. The filtrate and washings were combined, and the mixture was evaporated to dryness. The residue was chromatographed on a silica gel column (Kiesel gel 60, 40g) using chloroform-methanol (100:1-50:1) as eluant. Fractions containing the desired product were collected and evaporated to dryness. The residue was triturated with ether to give 255 mg (78%) of the title compound.

IR ν$_{max}$ (KBr) cm$^{-1}$ 1762, 1611, 1484, 1229, 1186, 1165.

UV λ$_{max\ (MeOH)}$ nm (ε) 285 (4,400).

$^1$H NMR (CDCl$_3$) δ4.95 (1H, d, J=8.1 Hz, H-1), 3.46 (1H, dd, J=8.1 and 3.0 Hz, H-2), 4.34 (1H, t, J=3.0 Hz, H-3), 3.37 (1H, dd, J=9.4 and 2.6 Hz, H-4), 3.89 (1H, ddd, J=10.3, 9.8 and 4.7 Hz, H-5), 3.53 (1H, t, J=10.3 Hz, Hax-6), 4.20 (1H, dd, J=10.3 and 4.7 Hz, Heq-6), 4.77 (1H, q, J=5.1 Hz, H-7), 1.39 (1H, d, J=5.1 Hz, H-8).

Anal. Calcd. for C$_{29}$H$_{32}$O$_{13}$: C 59.18, H 5.48. Found: C 59.18, H 5.51.

Example 2.
4'-Demethyl-4-O-(5,6-O-ethylidene-β-D-allofuranosyl)epipodophyllotoxin

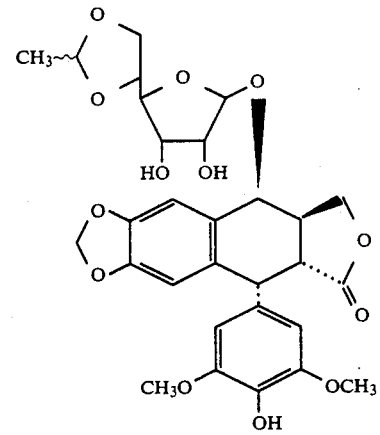

(a) Preparation of 4'-O-benzyloxycarbonyl-4'-demethyl-4-O-(2,3-di-O-benzyl-5,6-O-ethylidene-β-D-allofuranosyl)epipodophyllotoxin To a cooled (−22° C.) and stirred solution of 4'-O-benzyloxycarbonyl-4'-demethylepipodophyllotoxin (400 mg, 0.75 mmol) and compound F (440 mg, 1.14 mmol) in 30 ml of dry 1,2-dichloroethane was added boron trifluoride etherate (0.3 ml, 2.44 mmol), and the mixture was stirred at −22° C. for 30 minutes. Pyridine (0.2 ml) was added to the reaction mixture, and the mixture was stirred at −20° C. for 10 minutes, extracted with chloroform. The extract was washed with water and brine and dried over magnesium sulfate. The dried extract was evaporated to dryness, and the residue, including 2 isomers based on the ethylidene moiety, was separated by a silica gel column (Kiesel gel 60, 40 g). The column was eluted with toluene-ethyl acetate (5:1). The eluate was monitored with TLC (toluene ethyl acetate =2:1). The slower-moving fractions were collected and evaporated to dryness to give 290 mg (43%) of a first C-7″ epimer (compound G).

IR $\nu_{max}$ (KBr) cm$^{-1}$ 1771, 1602, 1484, 1235, 1132, 1039.

UV $\lambda_{max\ (MeOH)}$ nm ($\epsilon$) 292 (2800).

The faster-moving fractions were collected and evaporated to dryness to give 230 mg (34%) of a second C-7″ epimer (compound H).

IR $\nu_{max}$ (KBr) cm$^{-1}$ 1772, 1602, 1484, 1235, 1132, 1039.

UV $\lambda_{max\ (MeOH)}$ nm ($\epsilon$) 291 (3600).

(b) Preparation of 4′-demethyl-4-O-(5,6-O-ethylidene-β-D-allofuranosyl)epipodophyllotoxin Hydrogenation of compound G (270 mg) in the presence of 10% palladium on carbon gave 115 mg (65%) of the corresponding title compound (epimer I). MP 227°–229° C.

IR $\nu_{max}$ (KBr) cm$^{-1}$ 3440, 1780, 1615, 1484, 1230, 1123.

UV $\lambda_{max\ (MeOH)}$ nm ($\epsilon$) 285 (4600).

$^1$H NMR (CDCl$_3$) δ5.16 (1H br.s, H-1) 4.02 (1H, d, J=4.7 Hz, H-2), 4.35 (1H, dd, J=6.4 and 4.7 Hz, H-3), 3.97 (1H, t, J=6.4 Hz, H-4), 5.23 (1H, q, J=5.1Hz, H-7), 1.38 (1H, d, J=5.1 Hz, H-8).

Anal. Calcd. for C$_{29}$H$_{32}$O$_{13}$: C 59.18 H 5.48. Found: C 59.24, H 5.48.

Hydrogenation of compound H (210 mg) in the presence of 10% palladium on carbon gave 84 mg (61%) of the corresponding title compound (epimer II) as colorless crystals MP 160°–162° C.

IR $\nu_{max}$ (KBr) cm$^{-1}$ 1773, 1618, 1489, 1230, 1154.

UV $\lambda_{max\ (MeOH)}$ nm ($\epsilon$) 285 (4800).

$^1$H NMR (CDCl$_3$) δ5.16 (1H, br-s, H-1), 4.02 (1H, d, J=4.7 Hz, H-2), 4.37 (1H, dd, J=6.4 and 9.7 Hz, H-3), 3.93 (1H, t, J=6.4 Hz, H-4), 4.27 (1H, m, H-5), 3.97 (1H, dd, J =8.6 and 7.3 Hz, Hax-6), 4.06 (1H, dd, J=8.6 and 4.3 Hz, Heq-6), 5.06 (1H, q, J=4.7 Hz, H-7), 1.43 (1H, d, J=4.7 Hz, H-8).

Example 3.
4′-Demethyl-4-O-(4,6-O-ethylidene-β-D-mannopyranosyl)epipodophyllotoxin

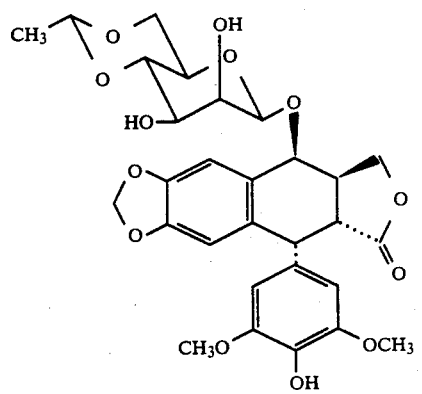

(a) Preparation of 4′-O-benzyloxycarbonyl-4′-demethyl-4-O-(2,3,4,6-tetra-O-acetyl-β-D-mannopyranosyl)epipodohyllotoxin and its α-anomer To a cooled (−15° C.) and stirred solution of 4′-O-benzyloxycarbonyl-4′-demethylepipodophyllotoxin (379 mg, 0.71 mmol) and 2,3,4,6-tetra-O-acetyl-D-mannopyranose (prepared according to the method described in K. Watanabe, et al., Carbohydr. Res., 1986, 154:165) (269 mg, 0.77 mmol) in 20 ml of dry 1,2-dichloroethane was added 0.27 ml (2.1 mmol) of boron trifluoride etherate, and the mixture was stirred at −15° C. for 30 minutes. To the mixture was added 0.5 ml of dry pyridine, and the mixture was stirred at −15° C. for 10 minutes. The mixture was washed with water and dried over anhydrous sodium sulfate. The organic phase was concentrated, and the residue was chromatographed on a silica gel column (1% MeOH-CH$_2$C1$_2$; monitored by TLC) to give 456 mg (74%) of 4′-O-benzyloxycarbonyl-4′-demethyl-4-O-(2,3,4,6-tetra-O-acetyl-D-mannopyranosyl)epipodophyllotoxin as an inseparable mixture of α- and β-anomers IR $\nu_{max}$ (KBr) cm$^{-1}$ 1730–1770 (broad), 1600.

$^1$H NMR (CDCl$_3$) δ2.02 and 2.18 (12H, each s, OCOCH$_3$×4), 3.67 (6H, s, OCH$_3$×2), 5.23 (2H, s, OCOCH$_2$Ph), 5.96 (2H, s, CH$_2$O$_2$), 6.23 and 6.28 (2H, each s, H-2′and 6′), 6.53 and 6.56 (1H, each s, H-8), 6.83 and 6.94 (1H, each s, H-5), 7.35 (5H, s, OCOCH$_2$Ph).

MS-EI m/z 864(M+).

(b) Preparation of 4′-O-benzyloxycarbonyl-4′-demethyl-4-O-(4,6-O-ethylidene-β-D-mannopyranosyl)epipodophyllotoxin and its α-anomer A mixture of the α- and β-anomers prepared in Step (a) above (430 mg, 0.5 mmol) and zinc acetate dihydrate (439 mg, 2.0 mmol) in methanol (20 ml) was refluxed for 4 hours with stirring, and the mixture was evaporated to dryness. The residue was diluted with chloroform (40 ml), i-propanol (10 ml), and acetic acid (0.2 ml), washed with water and aqueous sodium bicarbonate, and dried over anhydrous sodium sulfate. The organic phase was removed in vacuo to give 317 mg of a colorless semisolid of 4′-O-benzyloxycarbonyl-4′-demethyl-4-O-(D-mannopyranosyl)epipodophyllotoxin as a mixture of α- and β-anomers. This mixture, without purification, was subjected to the following ethylidenation.

To a stirred solution of the above semi-solid (247 mg, 0.35 mmol) and 1,1-dimethoxyethane (44 μl, 0.4 mmol) in dichloromethane (20 ml) was added one drop of concentrated sulfuric acid. The mixture was stirred at room temperature for 1 hour, washed with aqueous sodium bicarbonate and water, and dried over anhydrous sodium sulfate. The organic phase was evaporated in vacuo to give 270 mg of the 4'',6''-O-ethylidenated products as the crude semi-solid showing mainly 2 spots (Rf. value: 0.38 and 0.33, 4% MeOH-CH$_2$Cl$_2$) on TLC, which was separated repeatedly (2 times) on a silica gel column (3% MeOH-CH$_2$Cl$_2$, monitored by TLC) to give 38 mg of the β-anomer (Rf 0.38) and 69 mg of the α-anomer (Rf 0.33). The stereochemistry of the isomers at the C-1'' position was deduced from $^1$H NMR spectra of the deblocking products at the 4'-position.

(c) Preparation of 4'-demethyl-4-O-(4,6-O-ethylidene-β-D-mannopyranosyl)epipodophyllotoxin A mixture of the above β-anomer (38 mg) and 10% palladium on carbon (10 mg) in ethyl acetate (10 ml) was hydrogenated at an atm. After filtration of the catalyst, the filtrate was concentrated to give the crude product, which was chromatographed on Prep. TLC to give 26 mg of the title compound as colorless crystals. MP 235°-236° C.

IR $\nu_{max}$ (KBr) cm$^{-1}$ 3400, 1764, 1612.

UV $\lambda_{max\ (MeOH)}$ nm (ε) 238 (sh, 13,100), 286 (4,200).

$^1$H NMR (CDCl$_3$-DMSO-d$_6$) δ5.02 (1H, d, J=2.9 Hz, H-4), 4.77 (1H, q, J=5.1 Hz, H-7''), 4.72 (1H, d, J=0.7 Hz, H-1''), 4.59 (1H, dd, J=8.8 and 10.0 Hz, H-11), 4.55 (1H, d, J=5.5 Hz, H-1), 4.22 (1H, t, J=8.1 Hz, H-11), 4.17 (1H, dd, J=5.1 and 10.4 Hz, Heq-6'').

MS-FAB m/z 588 (M+).

Example 4.
4'-demethyl-4-O-(4,6-O-ethylidene-α-D-mannopyranosyl)epipodophyllotoxin

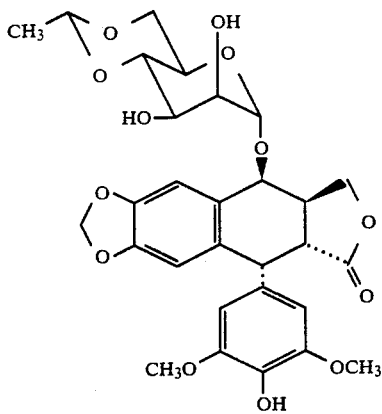

Hydrogenation according to the procedure of Example 3 step (c) of the α-anomer obtained in Example 3 step (b) (69 mg) afforded 45 mg of the title compound as colorless crystals. MP 286°-289° C.

Estimated purity 95% by HPLC.

IR $\nu_{max}$ (KBr) cm$^{-1}$ 3440, 1762, 1612.

UV $\lambda_{max\ (MeOH)}$ nm (ε) 238 (13,800), 285 (4,600).

$^1$H NMR (CDCl$_3$-DMSO-d6) δ4.95 (1H, d-like, J=<1 Hz, H-1''), 4.80 (1H, J=2.9 Hz, H-4), 4.74 (1H, q, J=5.1 Hz, H-7''), 4.58 (1H, d, J=5.5 Hz, H-1), 4.41 (1H, t, J=8.1 Hz, H-11), 4.11 (1H, dd, J=8.4 and 10.6 Hz, H-11), 4.00 (1H, dd, J=4.8 and 10.3 Hz, Heq-6'').

MS-FAB m/z 588 (M+).

We claim:
1. A compound having the formula:

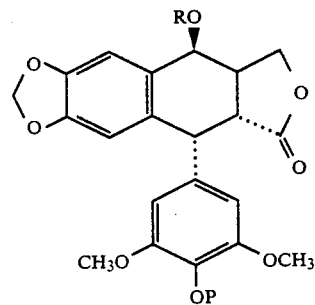

wherein R is selected from the group consisting of 4 6-O-alkylidene-β-D-allopyranosyl, 4,6-O-alkylidene-β-D-mannopyranosyl, 4,6-O-alkylidene-α-D-mannopyranosyl and 5,6-O-alkylidene-β-D-allofuranosyl; P is hydrogen or —PO$_3$H$_2$ or a pharmaceutically acceptable salt thereof.

2. A compound of claim 1 wherein R is 4,6-O-alkylidene-β-D-allopyranosyl.

3. A compound of claim 1 wherein R is 4,6-O-alkylidene-β-D-mannopyranosyl.

4. A compound of claim 1 wherein R is 5,6-O-alkylidene-β-D-allofuranosyl.

5. A compound of claim 1 which is 4'-demethyl-4-O-(4,6-O-ethylidene-β-D-allopyranosyl)epipodophyllotoxin.

6. A compound of claim 1 which is 4'-demethyl-4-O-(5,6-O-ethylidene-β-D-allofuranosyl)epipodophyllotoxin.

7. A compound of claim 1 which is 4'-demethyl-4-O-(4,6-O-ethylidene-β-D-mannopyranosyl)epipodophyllotoxin.

8. A compound of claim 1 which is 4'-demethyl-4-O-(4,6-O-ethylidene-α-D-mannopyranosyl)epipodophyllotoxin.

9. A pharmaceutical composition comprising a compound of claim 1 and a pharmaceutically acceptable vehicle.

* * * * *